US006433696B1

(12) United States Patent
Deiterman et al.

(10) Patent No.: US 6,433,696 B1
(45) Date of Patent: Aug. 13, 2002

(54) CARBON MONOXIDE EMITTING APPARATUS, CARBON MONOXIDE MONITOR SHUTOFF, AND CIRCUIT THEREFOR

(75) Inventors: Lenard Deiterman, Springdale, AR (US); Shawn Wright; John Morse, both of Westville, OK (US); Alfred H. Lemke, Siloam Springs, AK (US)

(73) Assignee: Alto U.S., Inc., Chesterfield, MO (US)

( * ) Notice: Subject to any disclaimer, the term of this patent is extended or adjusted under 35 U.S.C. 154(b) by 0 days.

(21) Appl. No.: 09/696,548

(22) Filed: Oct. 25, 2000

Related U.S. Application Data
(60) Provisional application No. 60/164,069, filed on Nov. 5, 1999.

(51) Int. Cl.$^7$ ............................................. G08B 17/10
(52) U.S. Cl. .................... 340/632; 340/633; 73/23.2; 73/23.3; 73/25.01; 702/24; 422/94; 422/98
(58) Field of Search ................. 340/632, 633, 340/634; 73/23.2, 23.31, 25.01; 422/94, 98; 702/24

(56) References Cited

U.S. PATENT DOCUMENTS

| | | |
|---|---|---|
| 4,067,004 A | 1/1978 | Gulbrantson |
| 4,390,869 A | 6/1983 | Christen et al. |
| 4,480,252 A | 10/1984 | Buonavita |
| 4,488,118 A | 12/1984 | Jeffers et al. |
| 4,490,715 A | 12/1984 | Kusanagi et al. |
| 4,630,038 A | 12/1986 | Jordan |
| 4,685,464 A | 8/1987 | Goldberger et al. |
| 4,688,021 A | 8/1987 | Buck et al. |
| 4,802,486 A | 2/1989 | Goodman et al. |
| 4,819,551 A | 4/1989 | Vole |
| 4,860,223 A * | 8/1989 | Grilk ........................ 340/632 |
| 4,896,143 A | 1/1990 | Dolnick et al. |
| 5,049,861 A * | 9/1991 | Grace et al. ................ 340/632 |
| 5,252,949 A | 10/1993 | Kirby et al. |
| 5,276,434 A | 1/1994 | Brooks et al. |
| 5,280,273 A | 1/1994 | Goldstein |
| 5,517,182 A | 5/1996 | Yasunaga et al. |
| 5,526,280 A | 6/1996 | Consadori et al. |
| 5,670,949 A | 9/1997 | Kirby et al. |
| 5,694,118 A | 12/1997 | Park et al. |
| 5,733,505 A | 3/1998 | Goldstein et al. |
| 5,764,150 A * | 6/1998 | Fleury et al. ................ 340/632 |
| 5,810,723 A | 9/1998 | Aldrich |
| 5,842,981 A | 12/1998 | Larsen et al. |
| 5,969,623 A | 10/1999 | Fleury et al. |
| 6,064,898 A | 5/2000 | Aldrich |
| 6,073,038 A | 6/2000 | Wang et al. |

FOREIGN PATENT DOCUMENTS

JP        8182666 A      7/1996

\* cited by examiner

*Primary Examiner*—Julie Lieu
(74) *Attorney, Agent, or Firm*—Senniger, Powers, Leavitt & Roedel

(57) ABSTRACT

A system for monitoring carbon monoxide in an environment which includes an apparatus emitting carbon monoxide, such as an internal combustion engine. A carbon monoxide sensor measures a concentration of carbon monoxide in the environment and provides an electrical signal to a processor that is representative of the measured concentration of carbon monoxide. The processor determines the concentration of carbon monoxide corresponding to the electrical signal, provides an output signal at or above predetermined carbon monoxide concentration thresholds, calculates an estimated carboxyhemoglobin level for the operator corresponding to the carbon monoxide concentrations calculated over time, and provides an output signal at or above predetermined carboxyhemoglobin thresholds. The signals are then received by one or more devices which provide textual, visual, and/or audible warnings indicating that environmental concentrations of carbon monoxide have caused a predetermined warning threshold to be met or exceeded. The signals may also be received by a device which shuts down the carbon monoxide generating apparatus.

48 Claims, 13 Drawing Sheets

CARBON MONOXIDE EMITTING APPARATUS, CARBON MONOXIDE MONITOR SHUTOFF, AND CIRCUIT THEREFOR

CROSS-REFERENCE TO RELATED APPLICATION

This application claims priority from U.S. provisional patent application Ser. No. 60/164,069, filed Nov. 5, 1999, the entire disclosure of which is incorporated herein by reference.

BACKGROUND OF INVENTION

1. Field of the Invention

The present invention relates generally to apparatus that emit carbon monoxide, carbon monoxide monitoring and, particularly, to a system for monitoring the presence of carbon monoxide in the environment and for providing a plurality of signals at various concentration levels, including a signal for shutting off the apparatus.

2. Description of Related Art

Carbon monoxide is an asphyxiant gas that is colorless, odorless, tasteless, and non-irritating. This gas is formed from incomplete combustion and is a well-known health hazard to humans which may cause discomfort, sickness, and even death. Common sources of carbon monoxide include fires, gas appliances, heaters and furnaces, internal combustion engines used in power equipment and vehicles, and so forth.

Carbon monoxide is particularly dangerous when present in enclosed areas, such as building interiors, where inadequate ventilation can result in a build up of carbon monoxide concentration. Common sources of carbon monoxide in industry are equipment powered by engines that are intended for indoor use. Some examples of these sources include forklifts, small vehicles and hand-operated equipment that are powered by small engines such as floor strippers and polishers. When internal combustion engines are operated indoors, carbon monoxide can rapidly accumulate even if the area appears to be well ventilated. Because carbon monoxide is colorless, odorless, tasteless, and nonirritating, it can overcome the exposed person without warning.

Carbon monoxide affects people primarily by binding to hemoglobin in the blood, thereby preventing the normal transportation of oxygen to the tissues (tissue hypoxia). Oxygen is normally transported to the tissues in the body by reversibly binding with hemoglobin present in red blood cells as blood circulates through the lungs. As the blood moves through the body, the hemoglobin releases the oxygen for use in the body tissues. The blood then returns to the lungs, where oxygen again binds to the hemoglobin and the process repeats itself.

Tissues that are sensitive to hypoxia, such as the brain, heart, and exercising muscle are most affected by carbon monoxide. When hemoglobin binds with carbon monoxide it forms carboxyhemoglobin. Hemoglobin has an binding affinity for hemoglobin that is approximately 250 times greater than its affinity for oxygen. Because of its higher binding affinity, once carbon monoxide is bound to the hemoglobin, unlike oxygen, it is not easily released. Breathing fresh air for three to four hours after being exposed to carbon monoxide only eliminates half of the carboxyhemoglobin in the blood. Thus, exposure to carbon monoxide forms carboxyhemoglobin, which prevents the binding of oxygen and reduces the oxygen-carrying capacity of the blood. This in turn may produce weakness and confusion, and may deprive the person of the ability to seek safety.

While carbon monoxide present in the air causes the formation of carboxyhemoglobin in the blood, it is the build-up of carboxyhemoglobin in the blood which causes the adverse health effects. Real-time monitoring of ambient carbon monoxide may be implemented to indicate hazardous carbon monoxide concentrations. This is useful to warn an individual who may otherwise be exposed to high concentrations of carbon monoxide for short periods of time (e.g., when an individual briefly walks through an area or room where high concentrations of carbon monoxide are present).

Monitoring real-time carbon monoxide concentrations does not, however, indicate whether a hazard is present due to the build-up of carboxyhemoglobin in the blood of an individual exposed to low concentrations of carbon monoxide during a work shift. This scenario is present when an individual is in an environment for extended periods of time such as during the operation of equipment with an internal combustion engine.

The EPA has reported that a variety of physical effects occur in humans at different levels of carboxyhemoglobin. At 80% carboxyhemoglobin—death. At 60%—loss of consciousness; death if exposure continues. At 40%—confusion; collapse upon exercise. At 30%—headache, fatigue, and impaired judgement. Between 7–20%—statistically significant decreased maximal oxygen consumption during strenuous exercise in healthy young men. Between 5–17%—statistically significant diminution of visual perception, manual dexterity, ability to learn, or performance in complex sensorimotor tasks (such as driving). Between 5–5.5%—statistically significant decreased maximal oxygen consumption and exercise time during strenuous exercise in young healthy men. Below 5%—no statistically significant vigilance decrements after exposure to carbon monoxide. Between 2.9–4.5%—statistically significant decreased exercise capacity (i.e., shortened duration of exercise before onset of pain) in patients with angina pectoris and increased duration of angina attacks. Between 2.3–4.3%—statistically significant decreased (about 3–7%) work time to exhaustion in exercising healthy men.

Unfortunately, recognizing early warning signs of carbon monoxide poisoning is often difficult because early symptoms (e.g., headache, dizziness, and nausea) are nonspecific and may be mistaken for symptoms of other illnesses such as colds, flu, or food poisoning. Because it is colorless, odorless, and nonirritating, carbon monoxide can overcome exposed persons without warning. Additionally, prior use of equipment without incident may give users a false sense of safety, reducing their awareness of potential exposure hazards.

Therefore, it is desirable to outfit internal combustion equipment designed to be operated indoors with carbon monoxide monitors that will warn individuals operating the equipment when carbon monoxide concentrations pose a health threat. Warning signals may take the form of lights, digital displays, audible alarms, and engine kill switches that can shut an engine off if carbon monoxide concentrations exceed a specified level. Such apparatuses have been disclosed in the prior art in the form of a carbon monoxide monitor attached to equipment possessing an internal combustion engine. Carbon monoxide monitors have also been equipped with timers which will set off alarms or shut off engines if a critical threshold of ambient carbon monoxide concentrations has been exceeded for a period of time. U.S. Pat. No. 5,276,434, the entire disclosure of which is incorporated herein by reference, discloses such a monitor. Prior art monitors, while attempting to consider exposure to low carbon monoxide concentrations over extended time periods, fail to accurately estimate the true hazards to equipment operators resulting from the build-up of carboxyhemoglobin in their blood.

A need therefore exists for a carbon monoxide monitoring system that can warn when carbon monoxide exposure presents a threat to an operator of internal combustion engine equipment. Such monitoring system is needed to monitor ambient carbon monoxide concentrations and to estimate the operator's carboxyhemoglobin level. Moreover, such monitoring system should provide comprehensive carbon monoxide monitoring, namely, indicating whether a hazardous situation exists from either short-term, high concentrations of carbon monoxide or extended exposures to low concentrations of carbon monoxide.

SUMMARY OF THE INVENTION

Accordingly, it is an object of the present invention to provide a comprehensive carbon monoxide monitoring system for use with an apparatus containing an internal combustion engine.

It is a more particular object of the present invention to provide a carbon monoxide generating apparatus such as a floor polisher powered by an internal combustion engine or a power washer with a heat chamber wherein fuel is burned and having a carbon monoxide monitoring system that warns of the presence of hazardous levels of carbon monoxide during the operation of the apparatus.

It is a further object of the present invention to provide a carbon monoxide monitoring system that measures carbon monoxide in the environment and estimates carboxyhemoglobin levels in the blood of an individual exposed to the environment.

Briefly, a system for monitoring carbon monoxide in an environment embodying aspects of the invention is for use with an apparatus containing an internal-combustion engine emitting carbon monoxide. The system includes a carbon monoxide sensor which samples the air and supplies an electrical signal representative of the concentration of carbon monoxide in the environment. The sensor supplies the electrical signal to a processor which calculates a corresponding concentration of carbon monoxide. If the concentration of carbon monoxide exceeds a threshold concentration, the processor provides an output signal to a device which then indicates the presence of carbon monoxide above the concentration threshold. The processor also calculates a time weighted average concentration corresponding to the concentrations of carbon monoxide that were measured over time. If the time-weighted average concentration exceeds a threshold, the processor provides an output signal to a device which then indicates the presence of carbon monoxide above the time-weighted average threshold.

In another aspect, the invention is directed to a carbon monoxide emitting apparatus equipped with a carbon monoxide monitor and an internal-combustion engine emitting carbon monoxide. The carbon monoxide monitor includes a carbon monoxide sensor that samples the air and supplies an electrical signal representative of the concentration of carbon monoxide in the environment. The sensor supplies the electrical signal to a processor which calculates a corresponding concentration of carbon monoxide. If the concentration of carbon monoxide exceeds a threshold concentration, the processor provides an output signal to a device which then indicates the presence of carbon monoxide above the concentration threshold. The processor also calculates a time weighted average concentration corresponding to the concentrations of carbon monoxide that were calculated over time. If the time-weighted average concentration exceeds a threshold, the processor provides an output signal to a device which then indicates the presence of carbon monoxide above the time-weighted average threshold.

In further aspect, the invention is directed to a carbon monoxide monitor. The carbon monoxide monitor includes a carbon monoxide sensor that samples the air and supplies an electrical signal representative of the concentration of carbon monoxide in the environment. The sensor supplies the electrical signal to a processor which calculates a corresponding concentration of carbon monoxide. If the concentration of carbon monoxide exceeds a threshold concentration, the processor provides an output signal to a device which then indicates the presence of carbon monoxide above the concentration threshold. The processor also calculates a time weighted average concentration corresponding to the concentrations of carbon monoxide that were calculated over time. If the time-weighted average concentration exceeds a threshold, the processor provides an output signal to a device which then indicates the presence of carbon monoxide above the time-weighted average threshold.

Other features of the present invention will be in part apparent to those skilled in the art and in part pointed out in the detailed description provided below.

BRIEF DESCRIPTION OF THE DRAWINGS

FIG. 9 is a schematic diagram of a power supply for a microcontroller board.

FIG. 10 is a non-volatile memory and external clock.

FIG. 11 is a tachometer and engine kill circuit.

FIG. 12 is a carbon monoxide sensor circuit.

FIG. 13 is a microcontroller circuit.

FIG. 14 is a LCD display and buzzer/horn circuit.

DETAILED DESCRIPTION OF PREFERRED EMBODIMENTS

Figure 1:
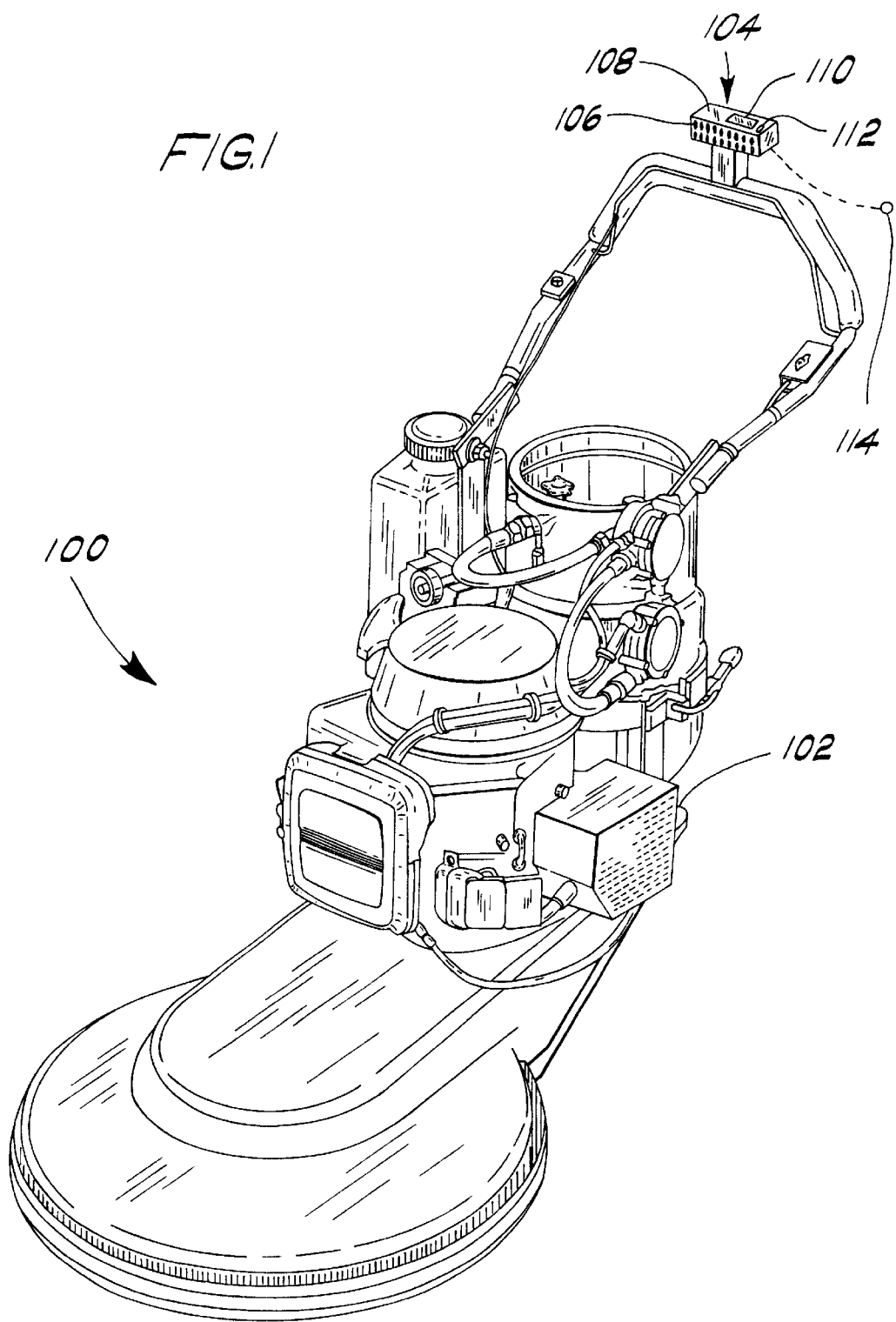
FIG. 1 is a illustration of a floor polisher apparatus of the walk-behind type powered by an internal combustion engine.

Referring now to the drawings, FIG. 1 shows a floor polisher 100, having an internal combustion engine 102. Floor polishers and strippers, such as the polisher 100, are common pieces of equipment that are normally operated indoors. Other industrial machines used indoors may also emit carbon monoxide without an internal combustion engine. An example of such a machine is a power washer that has a heat chamber in which a flammable or combustible fuel is burned. Since machines such as floor polishers 100, power washers, and other carbon monoxide producing machines are used indoors, they can pose a threat of carbon monoxide overexposure to their operators. It is this threat that the present invention is designed to prevent.

As an example, a variety of these units have polishing/stripping wheels powered by internal combustion engines that burn fuel such as gasoline or propane. The engine 102 emits carbon monoxide as a byproduct of incomplete combustion. An operator walking behind the polisher 100 would be subjected to carbon monoxide exposure while engine 102 is running. An illustrative embodiment of the present invention comprises a carbon monoxide monitoring system 104 being attached to the handle of polisher 100. The carbon monoxide monitoring system 104 consists of a perforated box 106. The perforated box 106 contains a carbon monoxide sensor. The perforated box 106 also contains alarm and data information equipment such as buzzer 108, LED display 110, and LCD display 112.

As internal combustion engine 102 operates, it generates carbon monoxide. Carbon monoxide gas diffuses and convects into the area surrounding the internal combustion engine 102. Carbon monoxide gas entering perforated box 106 is measured by the carbon monoxide sensor. LCD display 112 displays data relating to carbon monoxide concentration in the air. If an alarm condition is detected, buzzer 108, LED display 110, and LCD display 112 are activated, informing the operator of the alarm condition.

Figure 2:
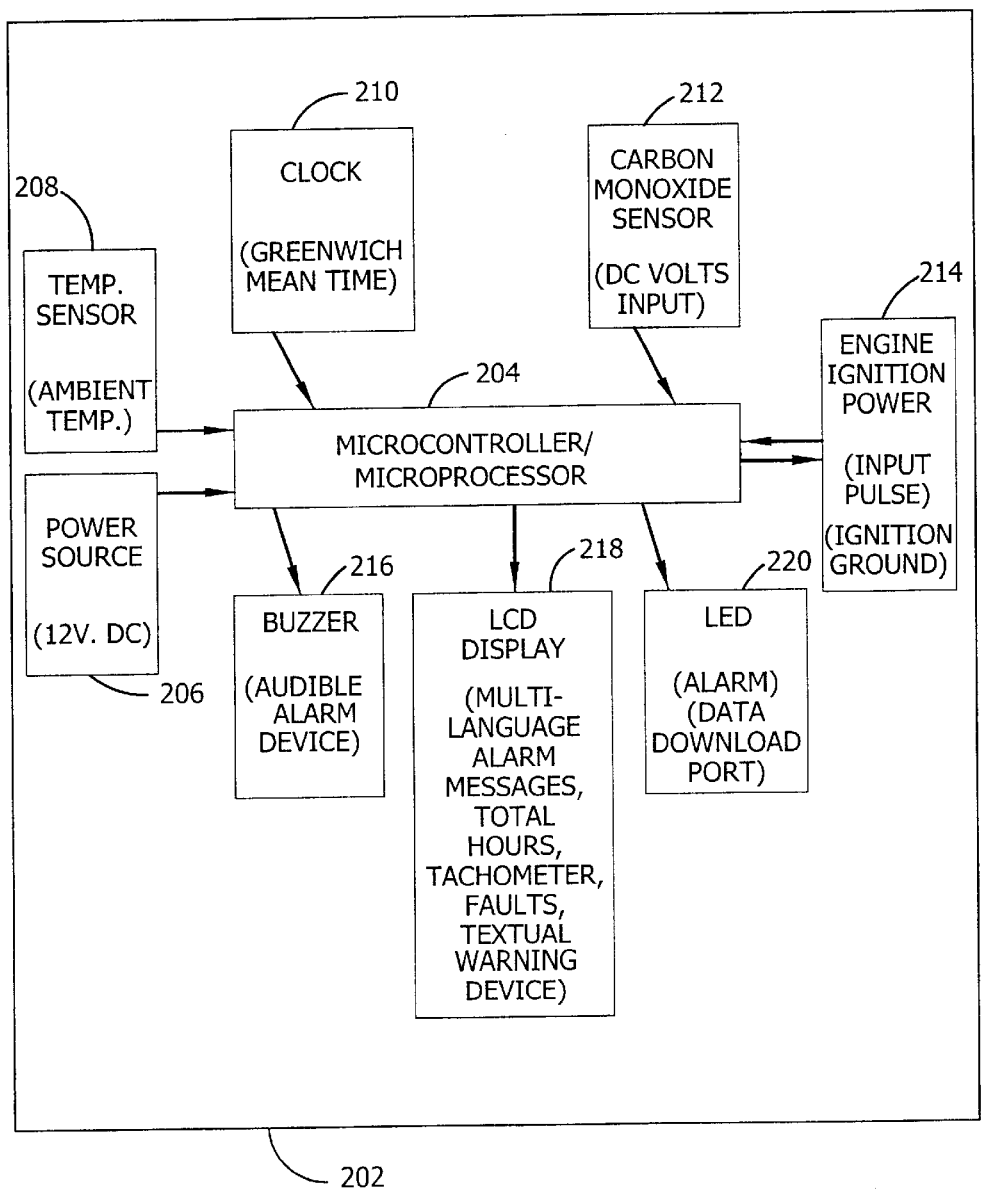
FIG. 2 is a block diagram of the carbon monoxide monitor according to a preferred embodiment of the inventor.

Referring to FIG. 2, an illustrative embodiment of a carbon monoxide monitoring system of the present invention is shown, designated generally as 202. The present invention shows a microprocessor or microcontroller 204 (hereinafter referred to as microcontroller) being supplied power by a DC power source 206. Microcontroller 204 has a plurality of pins which can be configured as digital inputs, outputs, or analog inputs. Microcontroller 204 receives data inputs from a temperature sensor 208, a battery powered real-time clock 210, a carbon monoxide sensor 212, and engine ignition power 214. Microcontroller 204 generates output signals to a plurality of devices, such as a buzzer/horn audible alarm 216, an LCD display 218 for providing alphanumeric information (e.g., alarm messages, concentration, total sampling hours, engine tachometer, system faults), and an LED display 220 for providing further alarm information as well as functioning as a data download port.

Figure 3:
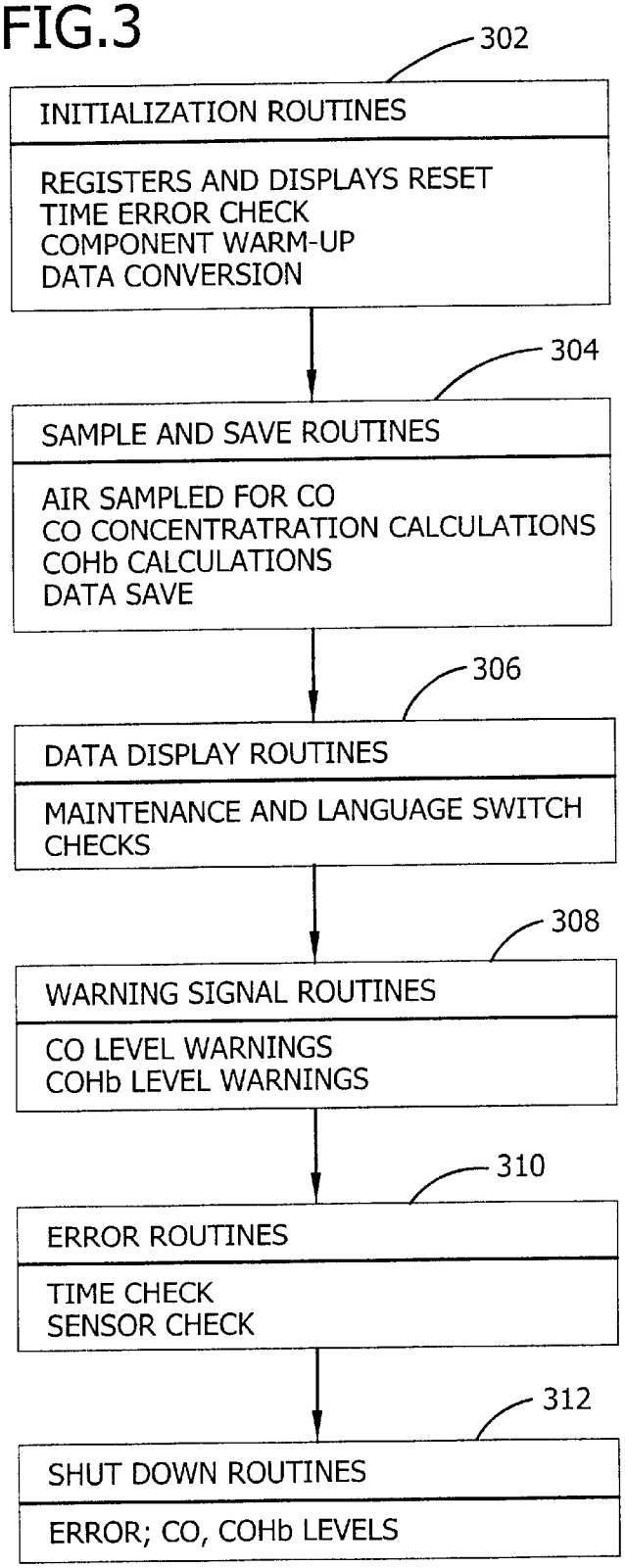
FIG. 3 is a block diagram of the general flowchart decision groups executed by the carbon monoxide monitor of FIG. 2.
Figure 4:
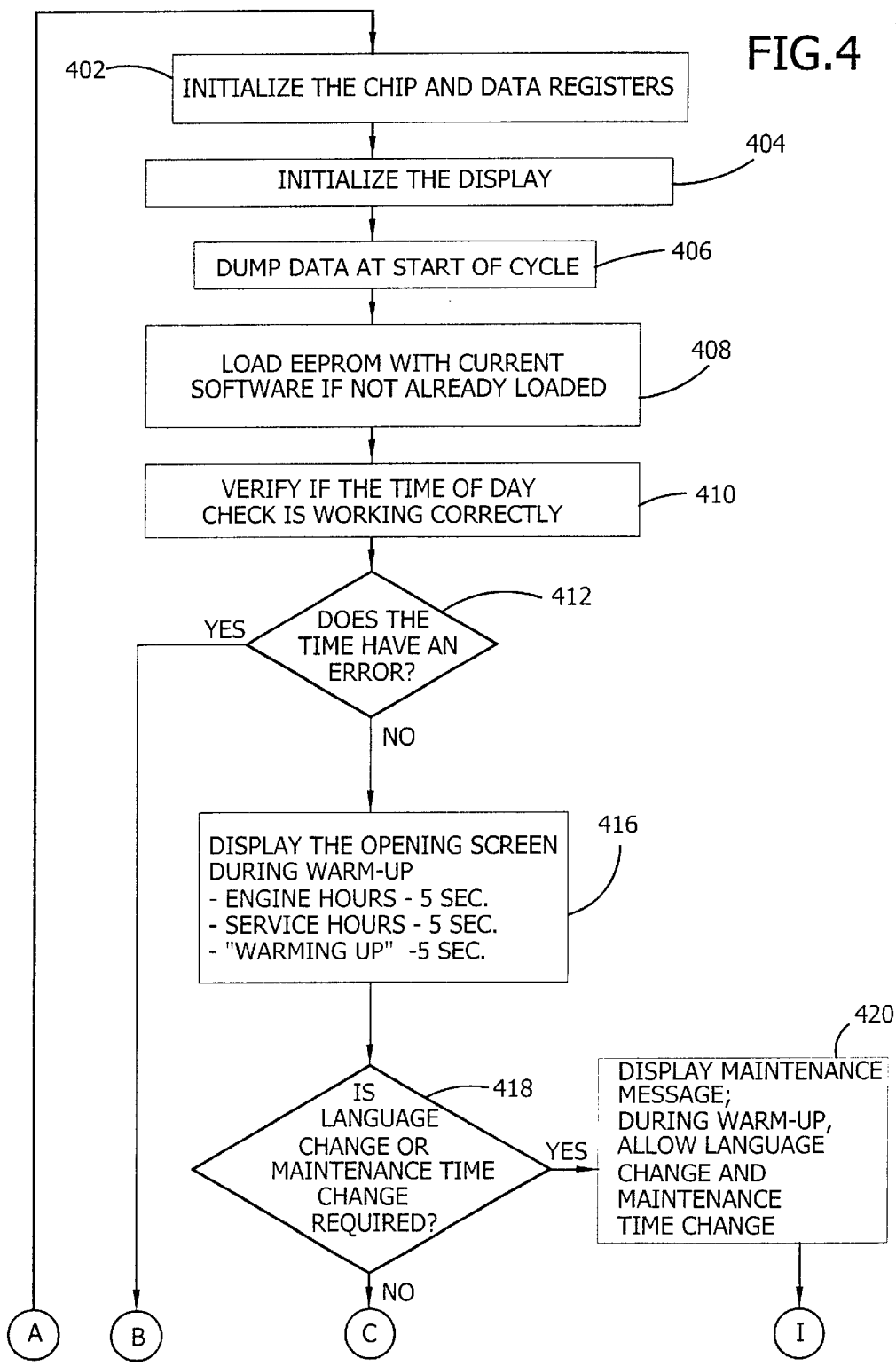
FIGS. 4–8 are flowcharts illustrating the decision steps of the invention as implemented by the various components shown in FIG. 2.

FIG. 3 describes an overview flowchart of the carbon monoxide sampling and alarm process. The process begins with initialization routines 302 which reset the registers of microcontroller 204 and displays 218 for receiving the initial sample data. In addition, the initialization routines 302 determine whether the clock 210 is functioning properly, warm up the carbon monoxide sensor 212, and determine whether to use data from the last time the monitor 202 was used. Next, the sample and save routines 304 are performed which sample the air, calculate carbon monoxide concentration and carboxyhemoglobin levels, and save the data to memory. Data display routines 306 then check the maintenance and language switches and display a message as necessary. Warning signal routines 308 next determine if an output signal should be provided that warns of a threshold level of carboxyhemoglobin or a threshold concentration of carbon monoxide being reached or exceeded. Error routines 310 are conducted which check the monitor's clock 210 and carbon monoxide sensor 212 for defects. Finally, shutdown routines 312 are performed if there are errors in monitor 202 or if the carboxyhemoglobin levels are greater than or equal to 20% or if the concentration of ambient carbon monoxide is greater than or equal to 500 ppm.

The flowcharts illustrated in FIGS. 4–8 provide the detailed decision steps of the invention. The process begins with step 402 in FIG. 4 when power source 206 applies power to monitor 202 thereby initializing the memory/processor chips and data registers of microcontroller 204. The processor then initializes the display in step 404. Data in the memory/processor chips and data registers is dumped in step 406. Step 408 next determines whether the EEPROM has had data written to it. If not, the EEPROM will then be initialized with the correct software version. At step 410, microcontroller 204 performs a time of day check to determine if clock 210 is functioning properly. If microcontroller 204 identifies an error in the time at step 412, the process branches to step 706 in FIG. 8. Otherwise, if microcontroller 204 does not identify an error, the process continues with step 416. At step 416, a LCD display 218 presents a start-up message. The start-up message includes displaying engine hours for five seconds, displaying service hours for five seconds, then display message "WARMING UP" for five seconds. Monitor 202 delays the sampling of carbon monoxide while sensor 212 warms up.

At decision step 418 microcontroller 204 determines if the display needs to be changed by checking the maintenance and language switches to determine if any have been pressed. If no switches have been pressed, the process continues at step 422 in FIG. 5.

If microcontroller 204 determines that the maintenance switch has been pressed, microcontroller 204 displays the maintenance message at step 420. Microcontroller 204 also determines if the language switch has been pressed. If it has, microcontroller 204 changes the specified language and updates the display. The process proceeds to step 422 in FIG. 5.

After the sensor has warmed up, at step 422, microcontroller 204 reads the current binary coded decimal (BCD) time and converts it to integer time. At step 424, the data saved in non-volatile memory (EEPROM) is retrieved. If it has been less than a predetermined period (e.g. eight hours or more) since this data was saved, the data is used to calculate the current level of carboxyhemoglobin. The time calculated in step 424 is saved in step 426 as the time the carboxyhemoglobin level was last calculated. At step 428, the raw data representing the sampled carbon monoxide is converted to a real number indicating the concentration of carbon monoxide in ppm. At step 430, the internal combustion engine 102 or other source of carbon monoxide, such as a fuel burner, is assumed to be operating during the rest of the process.

Figure 5:
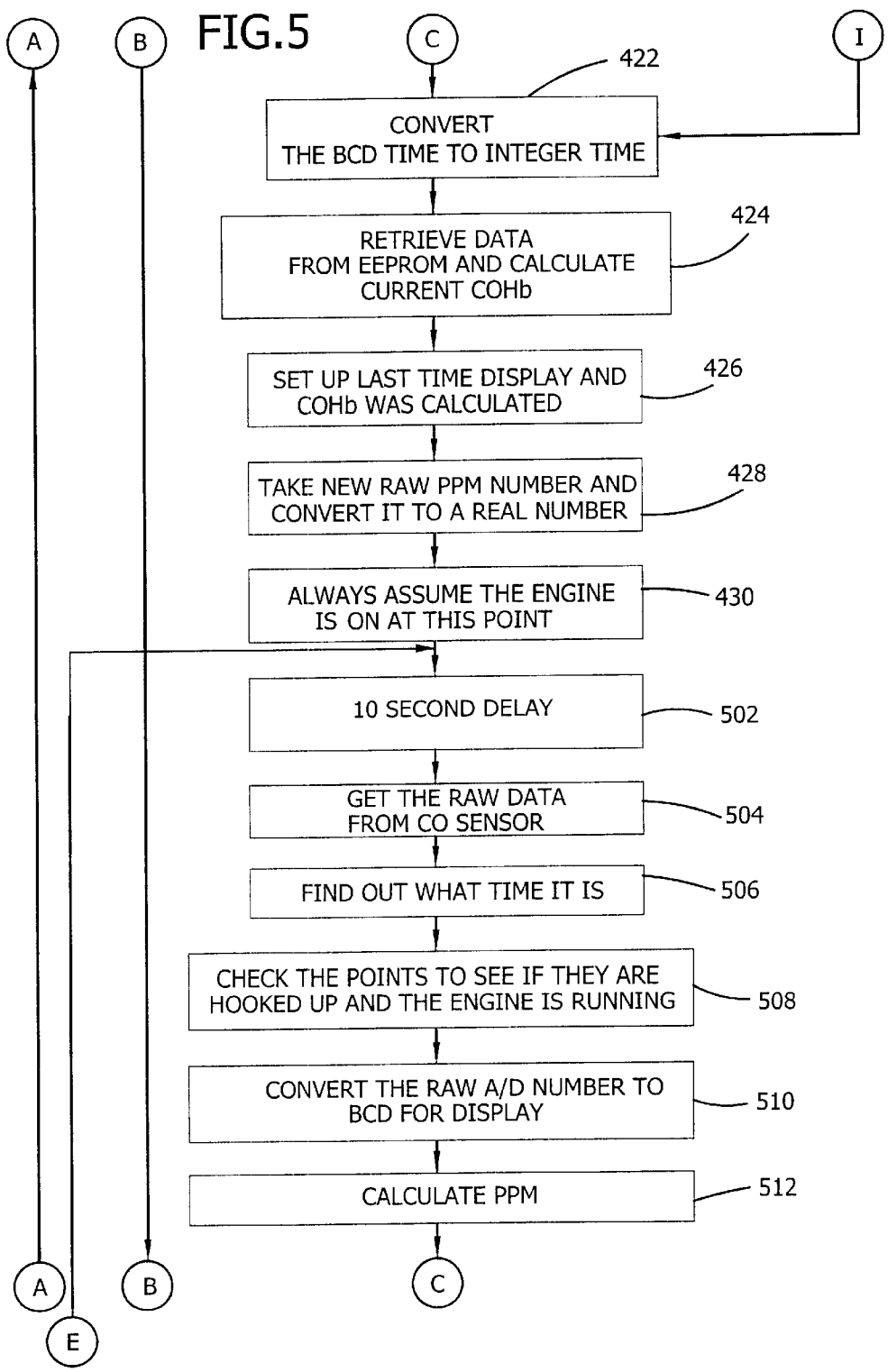
Figure 6:
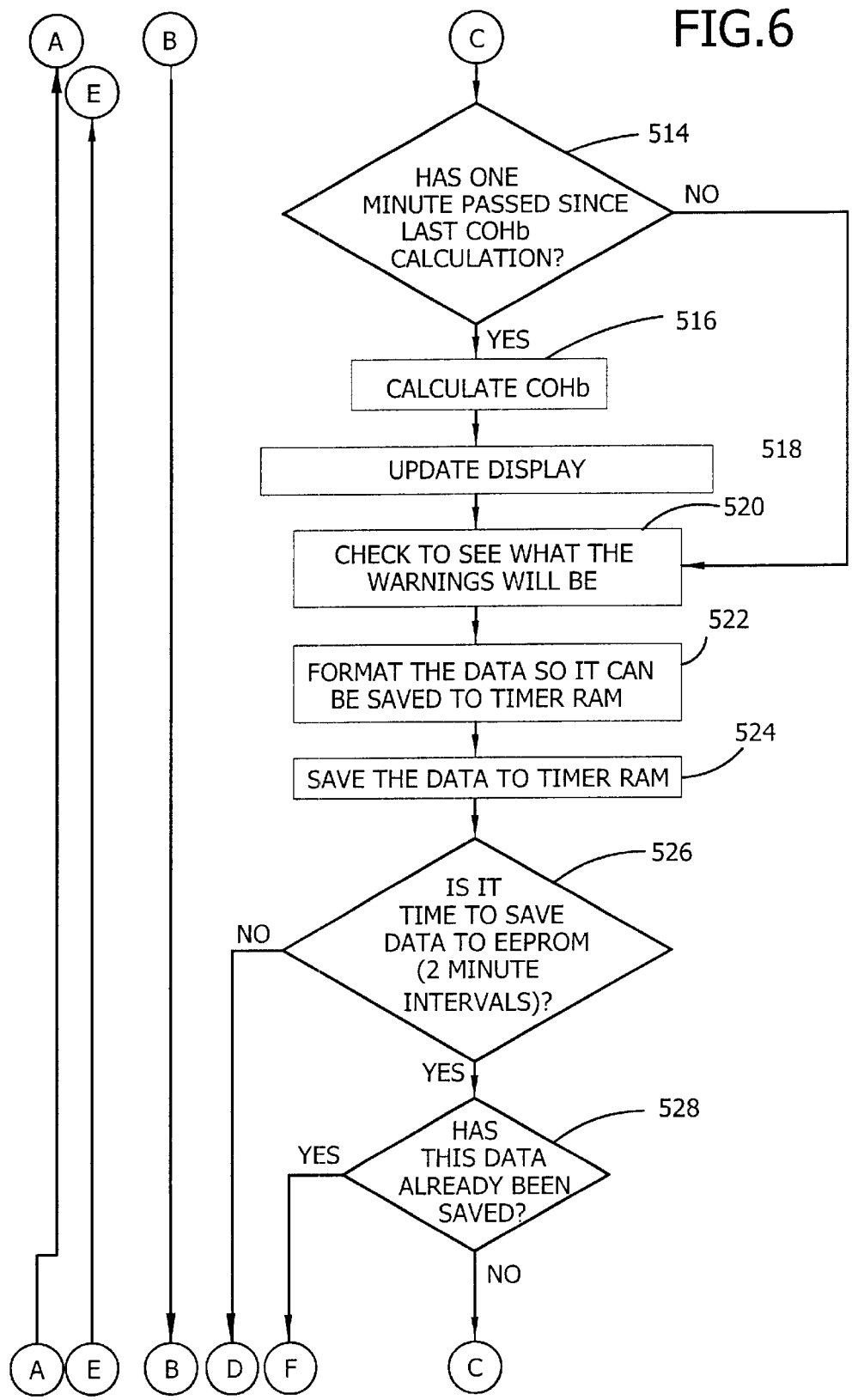

The process continues in FIG. 5 at step 502 where a ten second delay is executed. At step 504, carbon monoxide sensor 212 provides microcontroller 204 raw data from which the temperature and the carbon monoxide concentration is calculated. Microcontroller 204 determines the time from clock 210 at step 506. Microcontroller 204 tests points at step 508 to determine if they are connected and whether the internal-combustion engine or other combustion source is operating. Microcontroller 204 converts the analog data from the carbon monoxide sensor to a BCD digital number for display purposes in step 510. At step 512, microcontroller 204 converts the carbon monoxide digital number to a concentration value in ppm. At decision step 514 in FIG. 6, microcontroller 204, using the time from clock 210, calculates whether one minute has passed since the last carboxyhemoglobin calculation occurred. If one minute has passed, microcontroller 204 calculates the carboxyhemoglobin level in step 516, updates the display in step 518, and determines the appropriate warning signals at step 520. Otherwise, if in step 512 microcontroller 204 determines that one minute has not passed, microcontroller 204 proceeds directly to step 520 to determine the appropriate warning signals.

In step 522, microcontroller 204 formats the calculated carbon monoxide concentration, time, and carboxyhemoglobin data to enable it to be saved to the timer RAM and in step 524, microcontroller 204 saves the data to the timer RAM.

At decision step 526, microcontroller 204 determines the time from clock 210 to determine if the data should be saved to the EEPROM. If microcontroller 204 determines that a two minute interval has not passed since data was last saved, it proceeds to step 602 in FIG. 7. Otherwise, if at step 526, microcontroller 204 determines that a two minute interval has passed since data was last saved, at step 528 microcontroller 204 determines whether the data has already been saved to the EEPROM. If data has not already been saved, microcontroller 204 saves the data to the EEPROM at step 530 in FIG. 7 and continues to step 532. If at step 528, microcontroller 204 determines that the data has already been saved, no save will occur until the next interval and the process continues to step 532 in FIG. 7. At decision step 532, microcontroller 204 determines if language and maintenance time switches are closed. If both switches are closed, LCD display 218 displays "DEBUG" at step 534. The process continues to step 602.

At decision step 602, microcontroller 204 determines whether the warnings output signals have changed. If they have not, the process proceeds to step 606. If they have changed, microcontroller 204 activates the warning devices audible alarm 216, LCD display 218, and/or LED 220 at step 604 as necessary to provide audible, visual, or a combination of warning signals. At step 606, microcontroller 204 determines the carboxyhemoglobin level. If the carboxyhemoglobin level is 20% or greater, the process proceeds to step 706 in FIG. 8. If the carboxyhemoglobin level is below 20%, microcontroller 204 checks whether the concentration of carbon monoxide is 500 ppm or greater at step 608. If it is, the process proceeds to step 706 in FIG. 8. If the carbon monoxide concentration is less than 500 ppm, the process continues to step 702.

Figure 7:
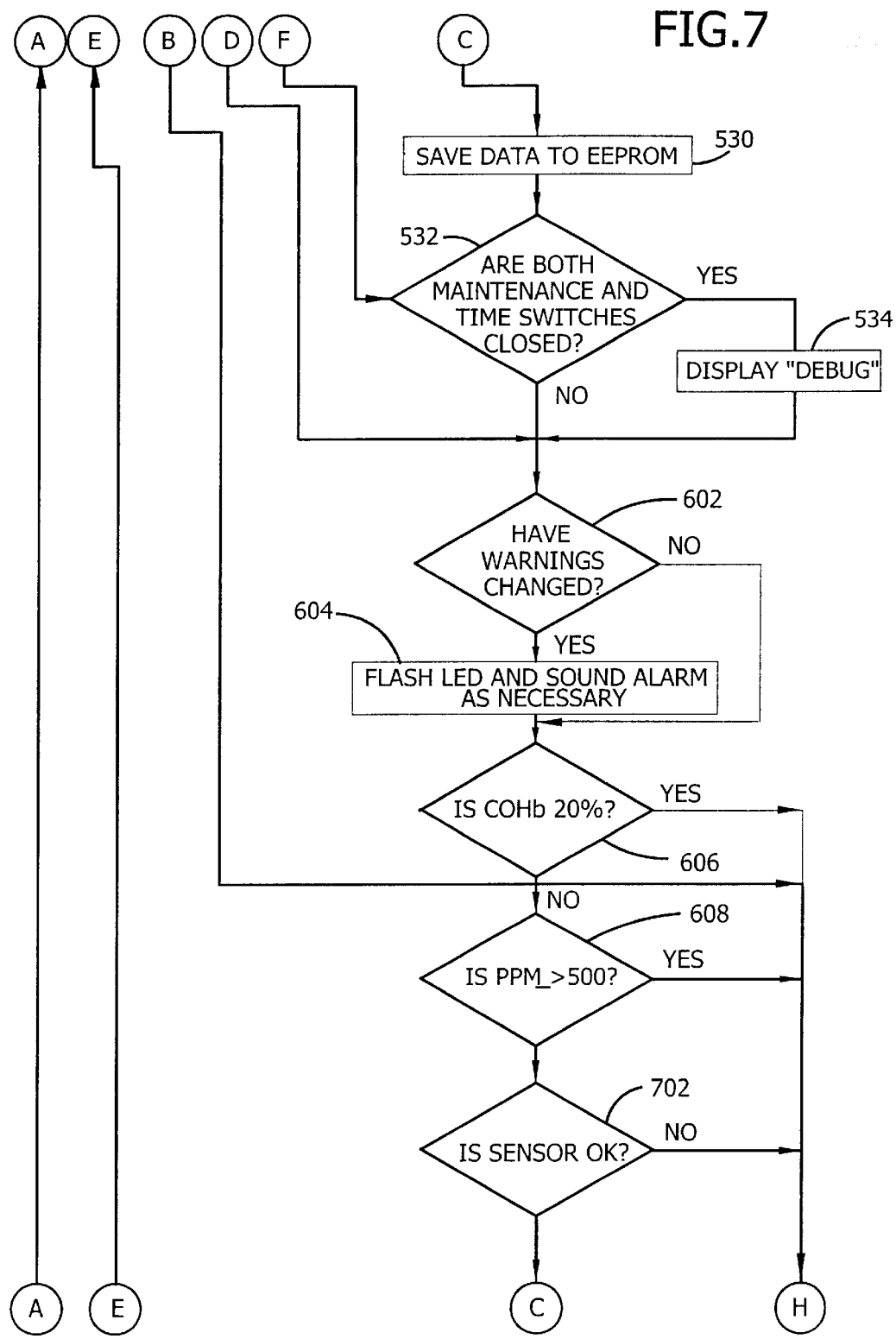
Figure 8:
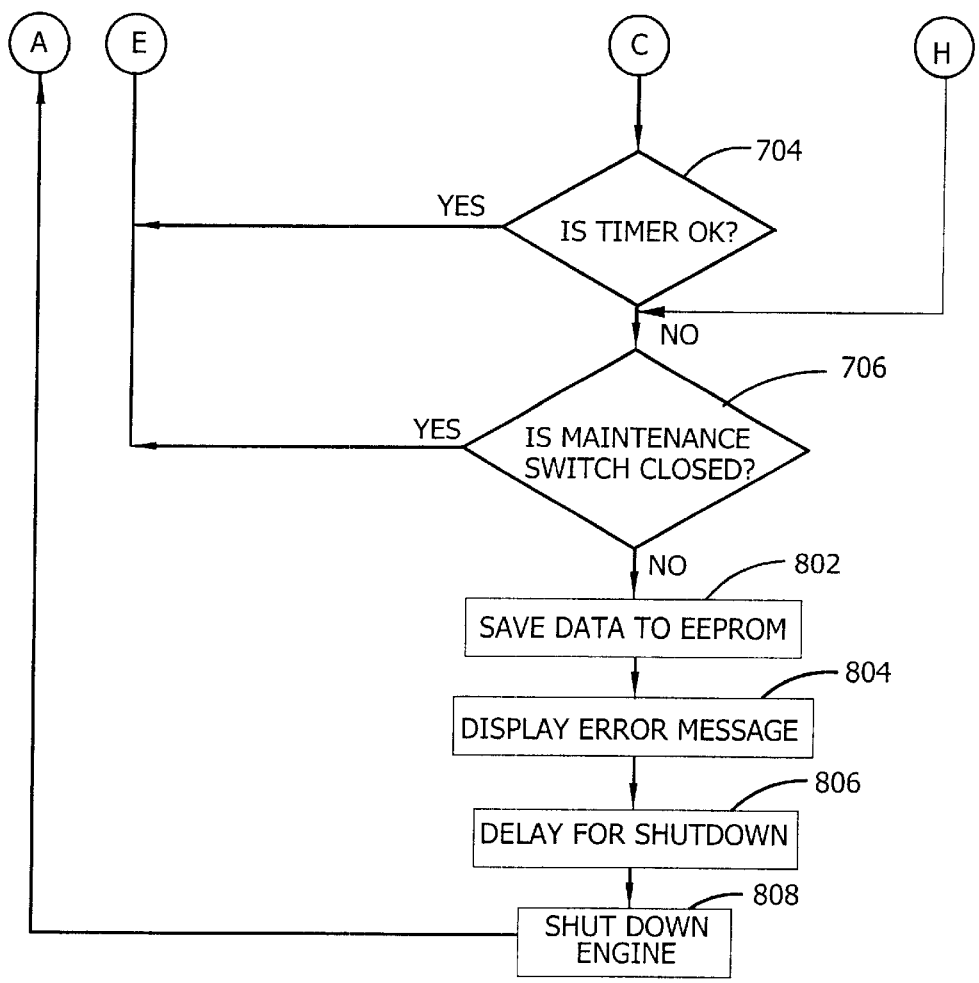

At step 702 in FIG. 7, microcontroller 204 checks the carbon monoxide sensor 212 to determine whether it is functioning properly. If carbon monoxide sensor 212 is operating correctly, microcontroller 204 checks clock 210 at step 804 to determine whether the timer is functioning properly. If the timer is operating correctly, the process repeats its cycle by proceeding to step 502 in FIG. 5.

If either carbon monoxide sensor 212 at step 702 or clock 210 at step 704 are determined to be malfunctioning, microcontroller 204 determines whether the maintenance switch is pressed at step 706. If the maintenance switch is pressed, the process repeats its carbon monoxide monitoring cycle by proceeding back to step 502 in FIG. 5. Otherwise, the process continues to step 802 wherein microcontroller 204 saves the current carboxyhemoglobin, carbon monoxide concentration, warning flags, time, and date data to the EEPROM. An error message is displayed at step 804 and an 18 ms shut down delay is initiated at step 806. Microcontroller 204 then shuts down the internal-combustion engine 102 by grounding engine ignition power 214 in step 808. Monitor 202 then returns to step 402 in FIG. 4 and restarts the process.

FIGS. 9–14 are schematic diagrams of a preferred embodiment of the invention. The schematics illustrate components of system 202 previously shown in block form in FIG. 2 in greater detail.

As described above, carbon monoxide sensor 212 detects carbon monoxide and provides microcontroller 204 with an analog voltage corresponding to the ambient carbon monoxide concentration. The sensor component has three electrodes for CO measurement: reference, working, and counter. The two operational amplifiers U1 and U2 shown in FIG. 12 attempt to hold the reference and working electrodes at virtual ground. If CO is present, a current is generated at the counter electrode. This current is transformed to a voltage level and amplified to provide the output of sensor 212. This signal is fed to an input of microcontroller 204.

Figure 13:
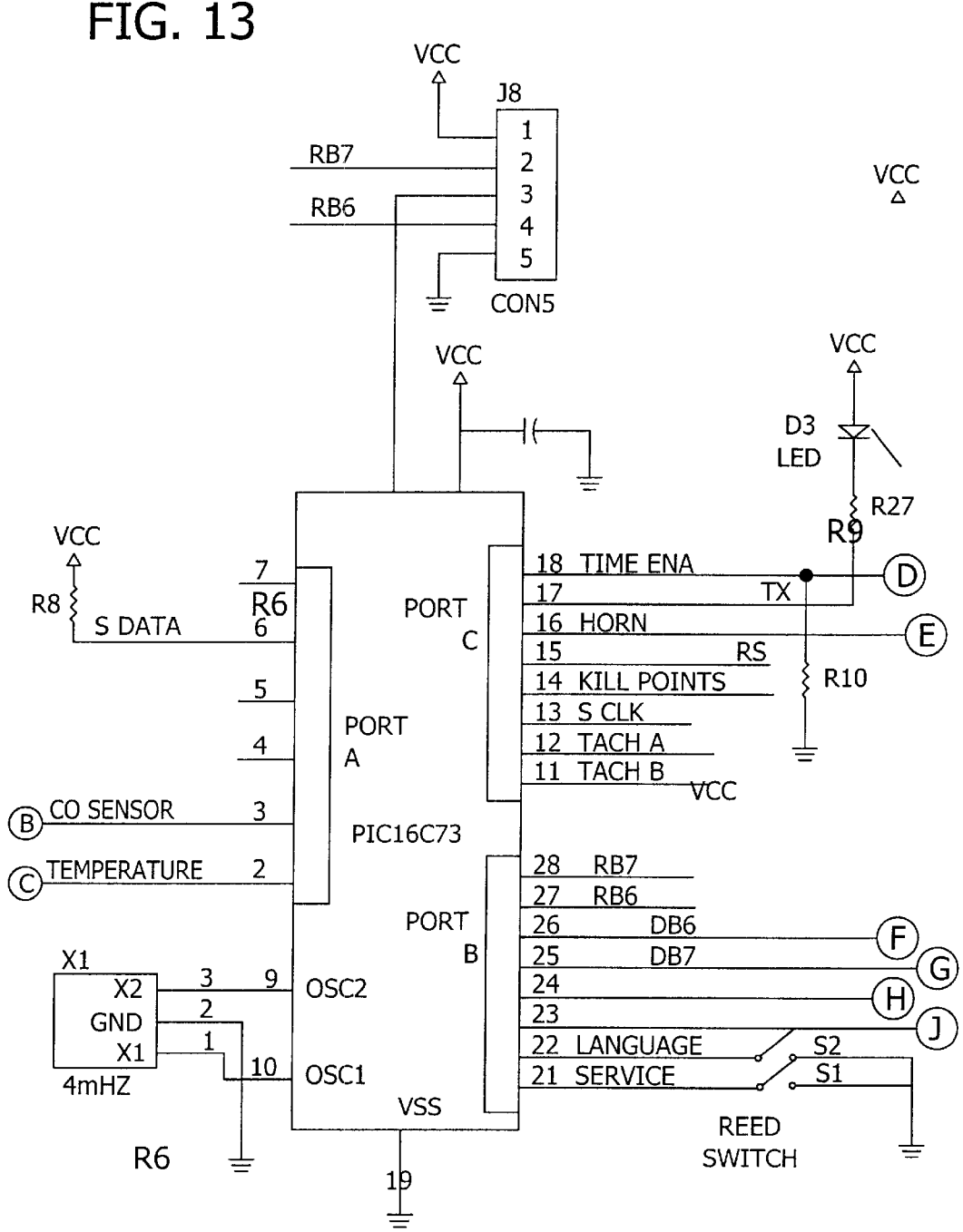
Figure 14:
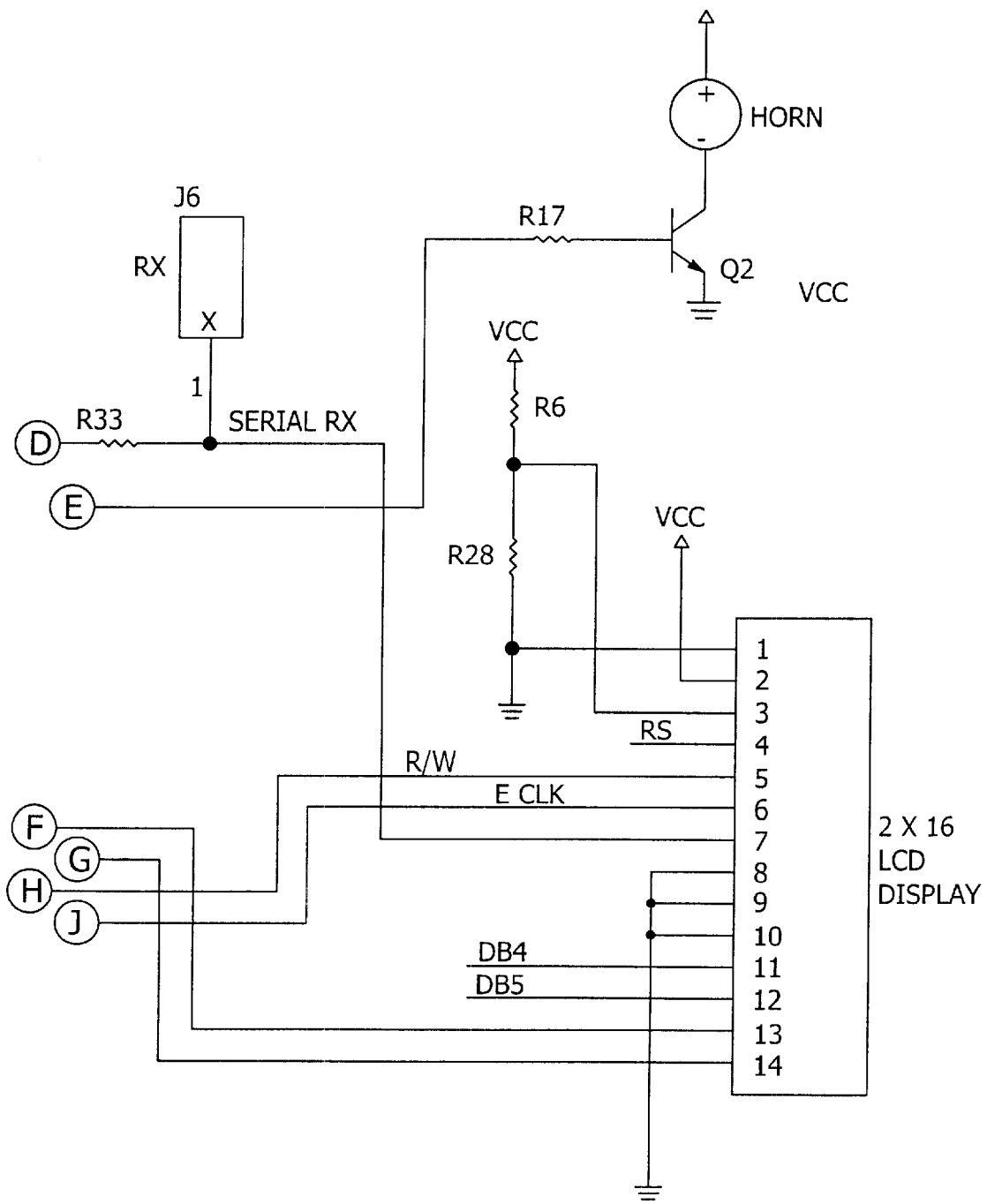

Microcontroller 204 is preferably an eight-bit device with internal ROM and analog inputs. Digital bits are provided which can be configured as either inputs or outputs, depending on the need. Microcontroller 204 also has a serial port for data communications. In FIG. 13, microcontroller 204 is designated as integrated circuit U2 having 28 pins, of which 21 can be configured as digital inputs, outputs, or analog inputs. Port A, bit 0 reads an analog voltage which represents the temperature. Port A, bit 1 reads the analog output voltage from carbon monoxide sensor 212. Microcontroller 204 later converts the output to a concentration in ppm. Port B, bits 0 and 1 are switch inputs. Port B, bits 2 through 7 are outputs to control the LCD display 218. Port C, bits 0 and 1 are tachometer inputs for speed and error detection. Port C, bit 2 receives the signal from the serial clock 210 embodied by a timekeeper integrated circuit U1 and the EEPROM U8. Port C, bit 3 is an output used to shut down the engine of floor polisher 100 or stop the burning of fuel in the heat chamber of a power washer. Port C, bit 5 is an output for the buzzer/horn audible alarm 216. Port C, bit 7 is an output to enable the timekeeper integrated circuit U1 (clock 210).

A tachometer 214 (FIG. 11) includes relay RY-1 which closes to shut down engine 102 under certain alarm conditions, such as high ambient carbon monoxide levels. It provides a direct short across the points of engine 102. The signal to operate the relay is provided by microntroller 204.

Circuitry is provided such that monitor 202 can determine if a wire to the points has been tampered with, which would prevent monitor 202 from shutting down engine 202. Tachometer 214 includes integrated circuit U5, consisting of U5A and U5B, which are open collector comparators that monitor the ignition points. If the signal from the points is not close to either zero volts or 12 volts, then microcontroller 204 assumes the points wire has been tampered with and issues an alarm condition and records the event in memory.

The timekeeper 210 (FIG. 10) is embodied by an integrated circuit U1 which is independently powered by a lithium battery. The timekeeper 210 generates data indicating the time of day, date, and year. The time data is necessary to identify when an alarm condition occurred as well as calculating time-weighted averages. The time, date, and year are stored in a non-volatile memory device (e.g. EEPROM U8 in FIG. 10) along with any warning signals that were output to the operator.

The LED 220 (also shown as D3 in FIG. 13) provides an alarm indicator when a problem is indicated by microcontroller 204. On a power up condition, however, microcontroller 204 reads the entire EEPROM U8 and outputs serial data to LED 220. The LED 220 blinks at a rate which is not apparent to the human eye. This enables a person with an appropriate serial device to read the output of LED 220 and retrieve or download information stored in memory U8. Thus, a record of the previous period or workshift of engine operation (e.g. eight or more hours), indicating whether the operator was warned, and the corresponding carbon monoxide levels with a time and date stamp may be obtained.

Figure 9:
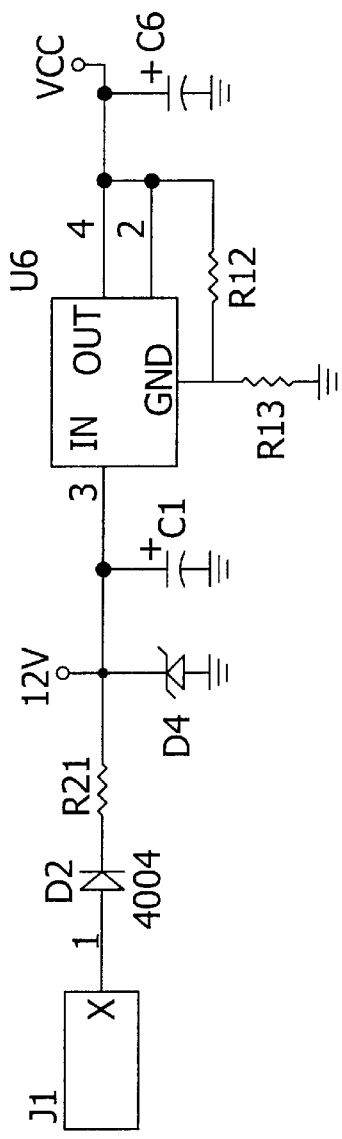
FIGS. 9–14 are schematic diagrams of a preferred embodiment of the carbon monoxide monitor of FIG. 2. A parts list for the parts contained in these figures is provided as Appendix A.
Figure 10:
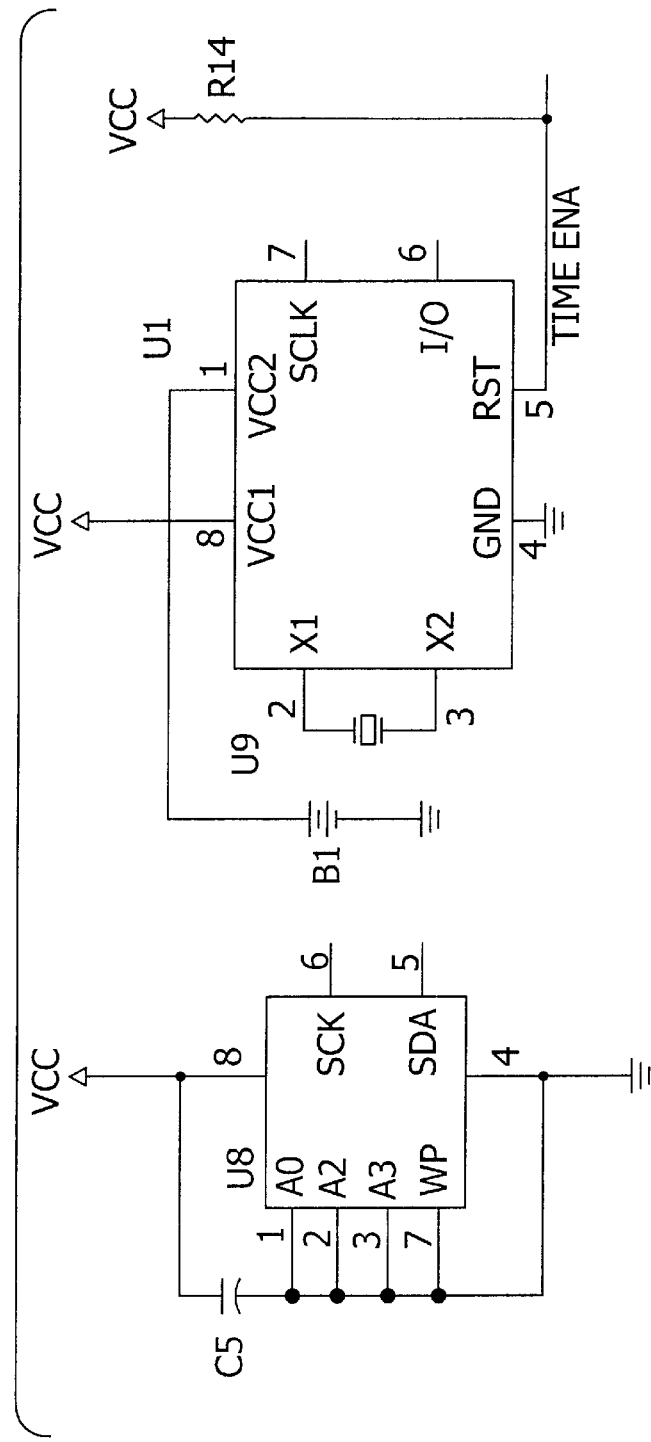
Figure 11:
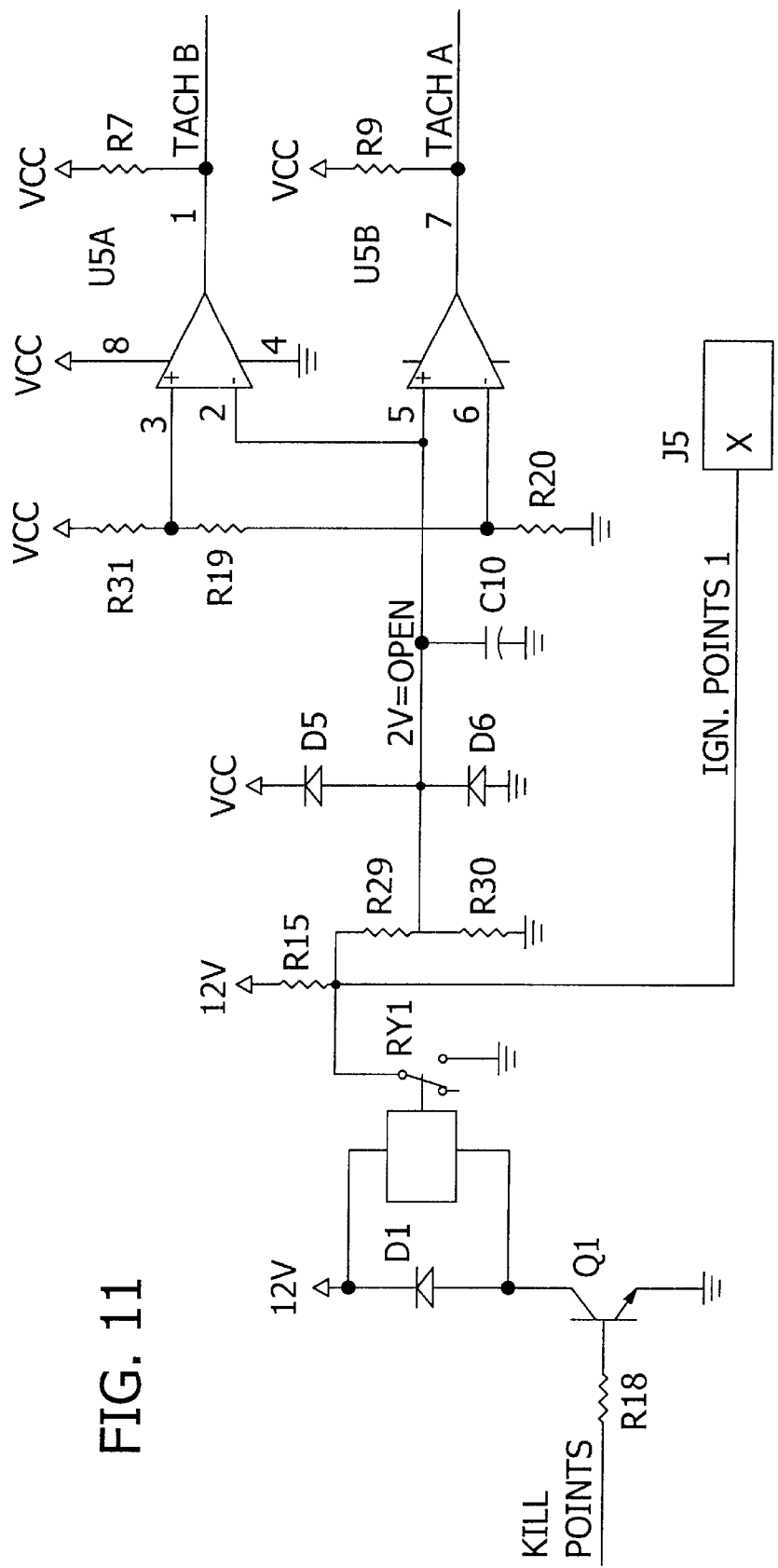
Figure 12:
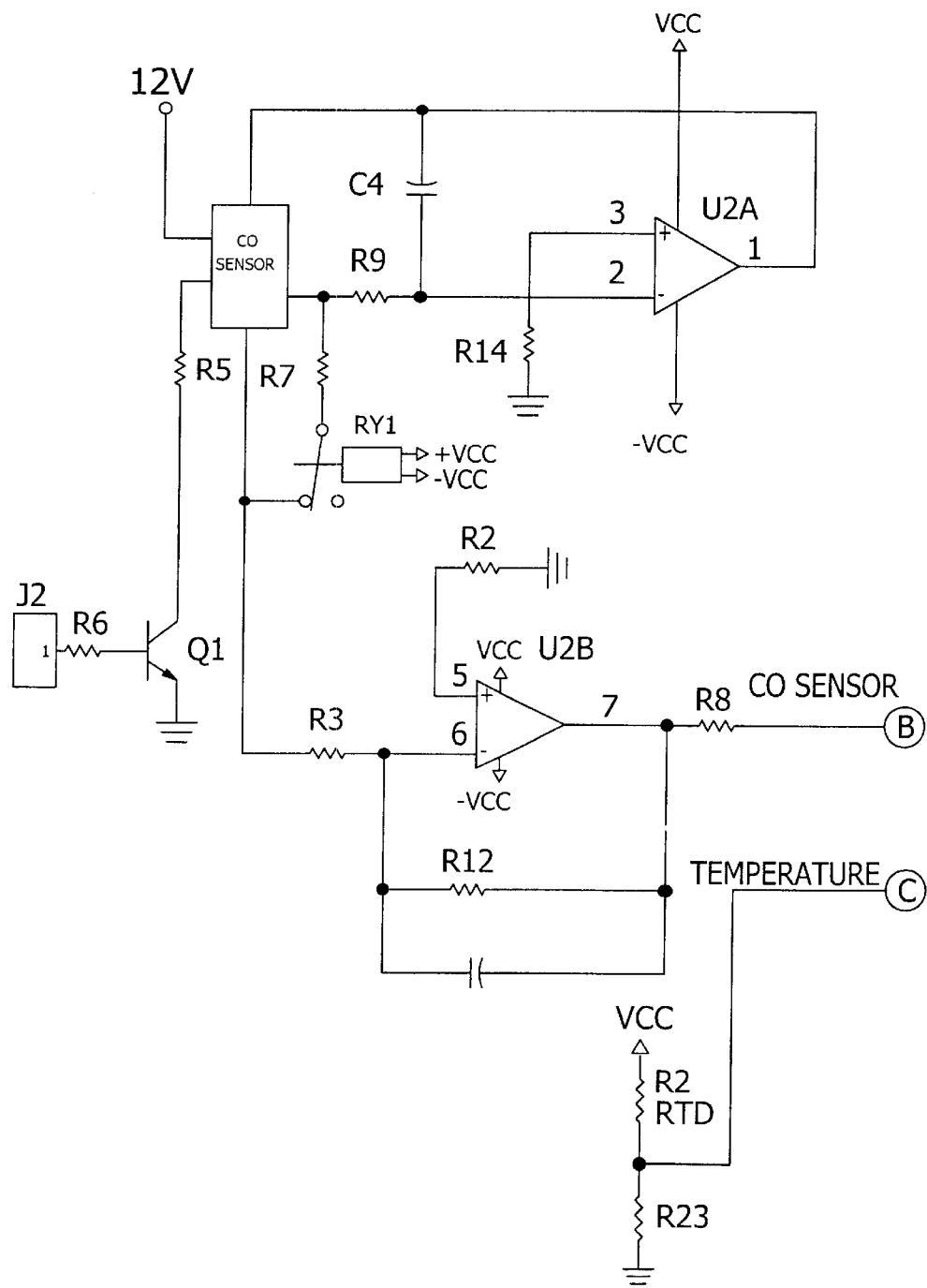

The power supply 206 is shown in FIG. 9 and includes a diode D2 providing reverse polarity protection and a diode D4 limiting the input voltage to a safe limit for a regulator U6. Regulator U6 regulates the 12 volt input and provides a stable 5 volt DC output. A capacitor C6 provides regulator stability and improves transient response.

One embodiment of the invention is therefore a carbon monoxide monitor and internal-combustion engine shutdown device. The carbon monoxide sensor 212 is preferably installed near the operator, e.g., on the handle of the equipment, at a location in which the ambient carbon monoxide concentrations approximate that of the air the operator breathes.

As described above, carbon monoxide sensor 212 takes ambient carbon monoxide readings and stores the raw data once per minute in a memory chip capable of holding sample results from a workshift (e.g. eight or more hours). Microcontroller 204 periodically analyzes the raw data to determine the carboxyhemoglobin level of the operator. The invention preferably emits signals to warn the operator if the carboxyhemoglobin levels are greater than or equal to 10%, 15%, and 20%.

Since the invention is controlled by microcontroller 204, many other functions in addition to monitoring carbon monoxide may be incorporated into the device. A non-exhaustive list of additional function examples include an hour meter, tachometer, multiple language text messages, resettable hours until engine service, count down timer, battery/charging system status, ambient carbon monoxide level, fuel mixture analysis via input from an oxygen sensor, ambient temperature, cylinder head temperature via thermocouple input, and real clock/calendar.

Data stored in the device's memory, (e.g., EEPROM U8), including unit serial number, production date, and so forth, can be retrieved with a photo-coupler placed over the LED 220 readout. A lithium battery backup of the memory will allow a minimum operation of approximately ten years.

In a preferred embodiment, monitor 202 includes three connections. These include connections to a 12 volt DC power source 206, to ground, and to the ignition 214 of the internal-combustion engine 102. The ignition connection is used as both an input and an output. When engine 102 starts, voltage pulses from the ignition coil(s) are received by the device, thereby confirming that the engine 102 is running. When microcontroller 204 decides to shut down the engine 102, the coil of a normally open relay is energized for approximately five seconds. One of the relay contacts is grounded and the other is connected to the ignition lead. Grounding the ignition lead "shuts-down" or "kills" engine 102.

The invention may include engines with different types of ignition systems. When engine 102 is revved up, microcontroller 204 determines if the particular engine type produces one or two pulses per revolution. Once the type of engine is determined, the invention uses the pulses on the ignition lead to perform a calculation of the engine's RPM.

When the device is not in a warning mode, the engine RPM, total accumulated engine time, hours until engine service, and so forth, will be displayed on LCD display 218.

The carbon monoxide monitor 202 preferably warns the operator at three progressively higher levels of carboxyhemoglobin or at excessive ambient concentrations of carbon monoxide. The first two levels audible alarm 216, turn on LED 220, and display a text message on display 218. The third level shuts off the engine 102 in addition to providing the alarm, LED signal, and text message. The warning levels of the preferred embodiment are 10%, 15%, and 20% blood carboxyhemoglobin levels and ambient concentrations of carbon monoxide is at or above 500 ppm. The device has the ability to calculate the carboxyhemoglobin levels and carbon monoxide exposure levels over a work shift (e.g. eight or more hours).

If the first level of warning is reached, e.g. 10% blood carboxyhemoglobin, audible alarm 216 will sound for two seconds, LED 220 will flash at a slow rate, and an appropriate text message will be displayed until the calculated carboxyhemoglobin level begins to decrease. Audible alarm 216 does not sound when the carboxyhemoglobin level descends. If the second level of warning is reached, e.g. 15% blood carboxyhemoglobin, audible alarm 216 sounds for four seconds, LED 220 flashes at a fast rate, and an appropriate text message will be displayed in LCD display 218 until the carboxyhemoglobin level decreases. As with the 10% warning, the alarm will not sound when the carboxyhemoglobin level descends. If the third level of warning is reached, LED 220 emits a steady light, display 218 displays an appropriate message, and audible alarm 216 sounds for 15 seconds, after which the engine 102 is shut down. After shut down, LED 220 remains on, the text message remains displayed, and audible alarm 216 sounds for one second every minute. To turn off LED 220, display 218 or audible alarm 216, power source 206 must be turned off.

A time-weighted average of ambient carbon monoxide concentrations is preferably taken and stored during the time engine 102 is running. If the device is operated, shut off for a time, and then restarted, microcontroller 204 estimates the carbon monoxide concentration data during the period of time the engine was not running. The carbon monoxide concentration is estimated from an average of the carbon monoxide concentration measured before the device was shut off and the carbon monoxide concentration measured when the device is restarted. If engine 102 has been off for a workshift period (e.g. eight or more hours), the data in memory will be zeroed out and a new day of operation will be initiated upon start up. Among other things, this means the initial carboxyhemoglobin level will be zero.

The carbon monoxide sensor component within sensor circuit 212 (Monox Electrochemical Sensor, Monox Limited, Wilts, U.K.) operates by catalytically converting CO molecules to carbon dioxide, and releases two hydrogen radicals at the working electrode. The counter electrode generates an electric current while forming water from the hydrogen radicals and ambient oxygen. A current of 80 nanoamps per ppm of carbon monoxide is generated.

In one embodiment, the output of sensor 212 passes through an analog to digital converter. The converter generates a digital number which represents the voltage across sensor 212. The analog to digital converter is, for example, an 8-bit converter with a resolution of 19.6 mV. The total range of the analog to digital converter is 0 to 255 which corresponds to a 0 to 5 V range.

The digital number is then used in the first order equation:

$$A*S-B = \text{ppm carbon monoxide}$$

A and B are constants determined for the sensor and S is the sensor signal. The constants are determined during calibration.

Preferably, a new carbon monoxide concentration is calculated every 15 seconds. If the concentration greater than 500 ppm, an alarm condition is given. If the concentration is not over 500 ppm and the reading is not the first reading in a minute, the reading is discarded. If the reading is the first reading in a minute, the reading is used to calculate the estimated level of carboxyhemoglobin in the operator. Microcontroller 204 calculates the carboxyhemoglobin level using the equation described in the UL 2034 carbon monoxide detector standard published Oct. 15, 1997. The equation is as follows:

$$\%COHbt = \%COHb0[e^{-(t/2398*B)}] + 218[1 - e^{-(t/2398*B)}][0.0003 + (PPM\ CO/1316)]$$

Wherein %COHbt is the percentage of carboxyhemoglobin at time t; %COHb0 is the percentage of carboxyhemoglobin in the blood at time 0; t is the time in minutes; and B is 0.0404 (wherein B is a variable used to calculate carboxyhemoglobin levels during different work efforts and 0.0404 is a value used for a heavy work effort). Once the carboxyhemoglobin level is determined, the value is stored. The carboxyhemoglobin level is calculated every minute. The last carboxyhemoglobin level calculated becomes the initial concentration (i.e. %COHb0) for the next calculation.

In another preferred embodiment, monitor 202 is equipped with look-ahead capability utilizing calculated carboxyhemoglobin levels of an operator. After the first alarm level has been reached (e.g. 10% carboxyhemoglobin level), microcontroller 204 calculates the amount of time before the carboxyhemoglobin level reaches the second alarm setpoint (e.g. 15% carboxyhemoglobin) using the current carbon monoxide reading and the current carboxyhemoglobin level. The calculation is made with the assumption that the current environmental carbon monoxide level will remain constant. Once the calculation is performed, display 218 displays a message stating the number of minutes remaining until the second alarm is triggered. The carboxyhemoglobin calculation will be made periodically and the displayed message will be updated in accordance with the latest calculation result.

The carboxyhemoglobin calculation is made using the following equation:

$$t = -2398*B*\ln[-1*(5.0E22*\%COHbt - 3.27E21 - 8.2826E21*ppmCO)/(-5.0E22*\%COHb0 + 3.27E21 + 8.2826E21*ppmCO)]$$

In this calculation, %COHbt is the setpoint carboxyhemoglobin level (e.g. 15% carboxyhemoglobin), %COHb0 is the current carboxyhemoglobin level, and ppmCO is the current carbon monoxide level in ppm. B is 0.0404, and t is the time in minutes.

After the second alarm stage is reached, a similar calculation will be made by microcontroller 204. The number of minutes remaining until the third alarm stage (e.g. 20% carboxyhemoglobin) will be calculated using the above formula. Microcontroller 204 will again assume that the current carbon monoxide level will remain constant. Display 218 displays a message stating the number of minutes until the machine is automatically shut down by monitor 202. This calculation will be made periodically and the displayed message will be updated in accordance with the latest calculation result.

In another embodiment, a carbon monoxide emitting apparatus, such as a floor polisher or power washer, can be equipped with an oxygen saturation sensor 114 which directly determines the oxygen saturation of an operator's blood as well as measure blood carboxyhemoglobin levels.

These sensors may be attached to the operator's finger, earlobe, bridge of the nose, or other part of the body enabling it to detect changes in the operator's blood. The data identifying oxygen saturation of the blood can be used to calculate the carboxyhemoglobin level of the operator's blood. Sensor 114 thus can be used in connection with carbon monoxide monitoring system 104 to warn the operator of increased blood carboxyhemoglobin levels as well as activate alarms or shut down the carbon monoxide emitting apparatus when predetermined carboxyhemoglobin levels are reached or exceeded.

Sensor 114 can also be utilized in connection with carbon monoxide monitoring system 104 to predict the amount of time an operator may continue to operate the apparatus without exceeding predetermined carboxyhemoglobin thresholds. For example, as the carboxyhemoglobin level begins to rise in an operator's blood, data such as the carboxyhemoglobin level and the rate the carboxyhemoglobin level is increasing can be used to calculate the time remaining that the carbon monoxide emitting apparatus may be operated without causing a threshold to be exceeded. One form of oxygen saturation sensors are referred to as pulse oximeters. Pulse oximeters operate by utilizing two LEDs for different wavelengths. The LEDs are fired at rates of up to 2000 Hz to permit light emitted from the LEDs to be differentiated from ambient light. One LED emits a light in the red wavelength range while the second LED emits light in the infrared range. A single detector reads levels of both wavelengths of light. The light in the red wavelength range is used to detect oxygenated blood as red wavelength light is strongly absorbed by oxygenated blood cells. The infrared light is used to measure total blood as infrared light is strongly absorbed by all blood cells regardless of their oxygenation state.

Electronic circuitry may be designed to change the amount of light produced by the LEDs to account for differences in path length, skin pigment, etc. in determining measurements. Measurement problems may occur due to movement of a pulse oximeter producing a "motion artifact" that interferes with its ability to detect when a pulse occurs. Motion may also disturb the path length between the LED and detector, thereby interfering with accurate measurements. Finally, the location in which the pulse oximeter is attached must be an area that is well perfused with blood to obtain accurate measurements.

Electronic circuitry determines when a pulse occurs and measures the ratio of oxygenated blood to total blood in a pulse. This ratio is the oxygen saturation level of the blood. Once the oxygenation level is determined, a level of carboxyhemoglobin may be estimated from the equation:

$$100\% - \text{oxygenation level } (\% O_2) = \% \text{ Carboxyhemoglobin}$$

In another embodiment, look-ahead capability is combined with use of a pulse oximeter (Nellcor N-20, Mallinckrodt, St. Louis, Mo.; Palco Oximeter Model 300, Scan Tech, Columbia, S.C.). After the first alarm stage (e.g. 10% carboxyhemoglobin) is reached, look-ahead calculations are performed. The processor subtracts the current oxygen saturation level from 100% to obtain the current carboxyhemoglobin level. Then the assumption is made that the current carbon monoxide level as measured by the carbon monoxide sensor will continue. Microcontroller 204 calculates how much time will elapse before the carboxyhemoglobin level reaches the second alarm setpoint (e.g. 15% carboxyhemoglobin). Display 218 displays a message stating the number of minutes remaining until the second alarm is triggered. The carboxyhemoglobin calculation will be made periodically and the displayed message will be updated in accordance with the latest calculation result. The calculation is made using the previously defined equation.

After the second alarm stage is reached, a similar calculation will be made by microcontroller 204. The number of minutes remaining until the third alarm stage (e.g. 20% carboxyhemoglobin level) will be calculated using the above formula, with 20% as the target setpoint. Microcontroller 204 will again assume that the current carbon monoxide level will remain constant. Display 218 displays a message stating the number of minutes until the machine is automatically shutdown by monitor 202. The carboxyhemoglobin calculation will be made periodically and the displayed message will be updated in accordance with the latest calculation result.

In further embodiment, a pulse oximeter is utilized with monitor 202. In this embodiment, the previously described predictive carboxyhemoglobin equation is not used. Instead, microcontroller 204 tracks the carbon monoxide levels and the carboxyhemoglobin levels and builds an empirical relationship between the quantities. The relationship is continuously refined using the applicable acquired data. Thus for a given operator on a given shift the carbon monoxide readings and carboxyhemoglobin readings can all be used in developing the empirical relationship. Each reading has a time step associated with it. Standard equation fitting techniques can be used to develop an equation from scratch, or the equation previously provided can be used as a basis. One method would be to fit a baseline carboxyhemoglobin level and also fit B, the work load variable. It is obvious that other equation fitting variations could also be used.

After the first alarm condition is reached, microcontroller 204 then calculates the time remaining until the second alarm condition (e.g. 15% carboxyhemoglobin) is reached. This time is calculated using the formula developed by the microcontroller 204. Display 218 displays a message stating how many minutes remain until then next alarm stage is reached.

After the second alarm stage is reached, a similar calculation will be made by monitor 202. The number of minutes remaining until the third alarm stage (e.g. 20% carboxyhemoglobin level) will be calculated, with 20% as the target setpoint. Microcontroller 204 will again assume that the current carbon monoxide level will remain constant. Display 218 displays a message stating the number of minutes until the machine is shutdown automatically by monitor 202. This calculation will be made periodically and the displayed message will be updated in accordance with the latest calculation result.

In view of the above, it will be seen that several objects of the invention are achieved and other advantageous results attained.

As various changes could be made in the above method without departing from the scope of the invention, it is intended that all matter contained in the above description be interpreted as illustrative and not in a limiting sense.

| DESCRIPTION | QTY | DESIGNATOR | SOURCE | NO. |
|---|---|---|---|---|
| BATT,3V | 1 | B1 | STOCK | |
| CAP,.1uF,0805 | 2 | C5,4 | STOCK | |
| CAP,1uF,3216 | 1 | C6 | STOCK | |
| CAP,220pF,0805 | 1 | C10 | STOCK | |
| CAP,330uF,35V | 1 | C1 | STOCK | |
| CER RES,4MHZ | 1 | X1 | STOCK | |
| CO SENS | 1 | U3 | STOCK | |
| DIO,DL4004,MLL41 | 2 | D1,2 | STOCK | |
| HDR,7 PIN,.100 | 2 | J4 | MOLEX | 22-03-2071 |
| HDR,4 PIN,.100 | 1 | J3 | MOLEX | 22-03-2041 |
| HDR,5 PIN,.100 | 2 | J8,7 | MOLEX | 22-03-2051 |
| IC,24C16 | 1 | U8 | MICROCHIP | 24LC16B/SN-ND |
| IC,DS1302,SO-8 | 1 | U1 | DALLAS | DS1302 SO-8 PKG |
| IC,LM393,SO-8 | 1 | U5 | DIGIKEY | LM393M-ND |
| IC,LMC6042,SO-8 | 1 | U4 | NATIONAL SEMI | LMC6042AIM |
| IC,PIC16C876 | 1 | U2 | MICROCHIP | 16F876-04/SP-ND |
| LCD,2X16,SERIAL | 1 | | OPTREX | DMC-16207U |
| LED,RED,T1 3/4 | 1 | D3 | DIGIKEY | P300-ND |
| PCB | 1 | | PLASTIC CKTS | N/A |
| PIEZO HORN | 1 | H1 | DIGIKEY | P9915-ND |
| POT,500K,1T | 1 | R26 | BOURNS | 3366W-504-ND |
| POT1,5K | 1 | R11 | BOURNS | 3366W-502-ND |
| REC,BAV70,SOT-23 | 2 | D5,6 | STOCK | |
| REG,LM317 EMP | 1 | U6 | STOCK | |
| RES,1.40K,0805 | 1 | R13 | STOCK | |
| RES,1.5K,0805 | 4 | R20,19,18,17 | DIGIKEY | P1.5KACT-ND |
| RES,100,0805 | 1 | R33 | DIGIKEY | P100ACT-ND |
| RES,10K,0805 | 5 | R6,9,10,7,8 | STOCK | |
| RES,15,1/4W,5%,CF | 1 | R21 | DIGIKEY | |
| RES,180K,0805 | 1 | R1 | DIGIKEY | P180KACT-ND |
| RES,2.49K,0805 | 1 | R31 | STOCK | |
| RES,220,0805 | 2 | R27,28 | DIGIKEY | P220ACT-ND |
| RES,3.0K,0805 | 1 | R23 | DIGIKEY | P3.0KACT-ND |
| RES,33K,0805 | 1 | R15 | DIGIKEY | P33KACT-ND |
| RES,4.02K,0805,1% | 1 | R2 | DIGIKEY | P4.02KCCT-ND |
| RES,475,1%,0805 | 1 | R12 | STOCK | |
| RES,47K,0805 | 2 | R14,25 | STOCK | |
| RES,750,0805,1% | 1 | R5 | DIGIKEY | P750CCT-ND |

-continued

| DESCRIPTION | QTY | DESIGNATOR | SOURCE | NO. |
| --- | --- | --- | --- | --- |
| RES,82K,0805 | 2 | R30,29 | DIGIKEY | P82KACT-ND |
| RLY,G5L,12V | 1 | RY1 | OMRON | G5LE-DC12 |
| SW,REED | 2 | S2 | STOCK | |
| THERM,3K | 1 | R24 | KEYSTONE | KC004N-ND |
| WIRE,BLK,18AWG | 3' | J2 | STOCK | |
| WIRE,GRY,18AWG | 3' | J5 | STOCK | |
| WIRE,RED,18AWG | 3' | J1 | STOCK | |
| XTL,32.768KHZ | 1 | U9 | DIGIKEY | X803-ND |
| XTR,MMBT4401,SOT-23 | 3 | Q1-3 | STOCK | |
| ZNR,33V,MLL34 | 1 | D4 | DIGIKEY | ZMM5257BCT-ND |

What is claimed is:

1. A system for monitoring carbon monoxide concentrations in an environment for use with an apparatus emitting carbon monoxide, said system comprising:
   a. a carbon monoxide sensor for measuring a concentration of carbon monoxide in the environment, said sensor providing a sensor signal representative of the measured concentration of carbon monoxide;
   b. a memory storing data relating to past carboxyhemoglobin levels;
   c. a processor receiving and responsive to the sensor signal for generating an output signal indicative of the concentration of carbon monoxide, said processor:
      i. receiving the sensor signal from the carbon monoxide sensor,
      ii. determining the concentration of carbon monoxide corresponding to the sensor signal,
      iii. retrieving the stored carboxyhemoglobin level data from the memory,
      iv. calculating a carboxyhemogolobin level corresponding to the determined concentration of carbon monoxide and the retrieved carboxyhemoglobin level data, and
      v. storing the calculated carboxyhemoglobin level to memory for a predetermined period of time while the apparatus is shut off for retrieval by the processor and calculation of subsequent carboxyhemoglobin levels.

2. The system of claim 1 wherein the sensor samples the carbon monoxide levels in the environment periodically.

3. The system of claim 1 wherein a determined concentration of carbon monoxide is stored to memory.

4. The system of claim 1 wherein a time-weighted average of ambient carbon monixide concentrations is calculated from an average of the carbon monoxide concentrations determined before the apparatus is shut off and the carbon monoxide concentration determined when the apparatus is restarted.

5. The system of claim 1 wherein the signal conditions can be retrieved from memory.

6. The system of claim 1 wherein an output signal will be provided to a warning device if the shut down device is unable to shut down the apparatus.

7. The system of claim 1 wherein the processor calculates a period of time remaining until a predetermined carboxyhemoglobin level is reached.

8. The carbon monoxide emitting apparatus of claim 1 wherein the apparatus is selected from the group consisting of a floor polisher and a power washer.

9. The system of claim 1 wherein the carboxyhemoglobin levels are calculated from the stored carboxyhemoglobin level data determined before the apparatus was shut off and the carbon monoxide concentration measured when the apparatus is restarted.

10. The system of claim 1 wherein the predetermined period of time is a workshift period.

11. The system of claim 10 wherein the workshift period is eight or more hours.

12. The system of claim 1 wherein an output signal is provided at or above a specified carbon monoxide concentration or carboxyhemoglobin level threshold, the output signal activating a device selected from the group consisting of an analog display, digital display, light emitting device, sound emitting device, shut-down device for the apparatus, or combination thereof.

13. The system of claim 12 wherein an output signal is not provided if the estimated level of carboxyhemoglobin exceeds a threshold carboxyhemoglobin concentration and the estimated level of carboxyhemoglobin is less than the immediately preceding estimated level of carboxyhemoglobin.

14. The system of claim 12 wherein the conditions causing the output signal to be provided are stored to memory.

15. The system of claim 12 wherein the device displays a message stating a period of time until the apparatus is automatically shut down.

16. A carbon monoxide emitting apparatus having a carbon monoxide monitor for measuring carbon monoxide in an environment, said apparatus comprising:
   a. a carbon monoxide monitor comprising:
      i. a carbon monoxide sensor for measuring a concentration of carbon monoxide in the environment, said sensor providing a sensor signal representative of the measured concentration of carbon monoxide;
      ii. a memory storing data relating to past carboxyhemoglobin levels;
      iii. a processor receiving and responsive to the sensor signal for generating an output signal indicative of the concentration of carbon monoxide, said processor:
         (1) receiving the sensor signal from the carbon monoxide sensor,
         (2) determining the concentration of carbon monoxide corresponding to the sensor signal,
         (3) retrieving the stored carboxyhemoglobin level data from the memory,
         (4) calculating a carboxyhemoglobin level corresponding to the determined concentration of carbon monoxide and the retrieved carboxyhemoglobin level data,
         (5) storing the calculated carboxyhemoglobin level data to the memory for a predetermined period of time while the apparatus is shut off for retrieval by the processor and calculation of subsequent carboxyhemoglobin levels, and (6) providing an output signal at or above specified carboxyhemoglobin concentration thresholds; and
b. a device that indicates the output signal.

17. The carbon monoxide emitting apparatus of claim 16 wherein the sensor samples the carbon monoxide levels in the environment periodically.

18. The carbon monoxide emitting apparatus of claim 16 wherein a determined concentration of carbon monoxide is stored to memory.

19. The carbon monoxide emitting apparatus of claim 16 wherein an output signal is not provided by the processor if the estimated level of carboxyhemoglobin exceeds a threshold carboxyhemoglobin concentration and the estimated level of carboxyhemoglobin is less than the immediately preceding estimated level of carboxyhemoglobin.

20. The carbon monoxide emitting apparatus of claim 16 wherein the device is selected from the group consisting of an analog display, digital display, light emitting device, sound emitting device, shut-down device for the apparatus, or combination thereof.

21. The carbon monoxide emitting apparatus of claim 16 wherein the apparatus is selected from the group consisting of a floor polisher and a power washer.

22. The carbon monoxide emitting apparatus of claim 16 wherein the processor calculates a period of time remaining until a predetermined carboxyhemoglobin level is reached.

23. The carbon monoxide monitor of claim 16 wherein an output signal is provided at or above a specified carbon monoxide concentration threshold, the output signal activating a device selected from the group consisting of an analog display, digital display, light emitting device, sound emitting device, shut-down device for the apparatus, or combination thereof.

24. The carbon monoxide emitting apparatus of claim 16 wherein the time-weighted average of ambient carbon monoxide concentrations is calculated from an average of the carbon monoxide concentrations determined before the apparatus was shut off and the carbon monoxide concentration determined when the apparatus is restarted.

25. The carbon monoxide emitting apparatus of claim 16 wherein the carboxyhemoglobin levels are calculated from the stored carboxyhemoglobin level data determined before the apparatus was shut off and the carbon monoxide concentration measured when the apparatus is restarted.

26. A carbon monoxide monitor comprising:
a. a carbon monoxide sensor for measuring a concentration of carbon monoxide in the environment, said sensor providing a sensor signal representative of the measured concentration of carbon monoxide;
b. a memory storing data relating to past carboxyhemoglobin levels;
c. a processor receiving and responsive to the sensor signal for generating an output signal indicative of the concentration of carbon monoxide, said processor:
  i. receiving the sensor signal from the carbon monoxide sensor,
  ii. determining the concentration of carbon monoxide corresponding to the sensor signal,
  iii. retrieving the stored carboxyhemoglobin level data from the memory,
  iv. calculating a carboxyhemoglobin level corresponding to the determined concentration of carbon monoxide and the retrieved carboxyhemoglobin level data,
  v. storing the calculated carboxyhemoglobin level data to memory for a predetermined period of time while the apparatus is shut off for retrieval by the processor and calculation of subsequent carboxyhemoglobin levels, and
  vi. providing an output signal at or above specified carboxyhemoglobin concentration thresholds;
d. a device that indicates the output signal; and
e. electrical leads adapted to receive and transfer data between the carbon monoxide monitor and equipment powered with internal-combustion equipment that emits carbon monoxide.

27. The carbon monoxide monitor of claim 26 wherein the sensor samples the carbon monoxide levels in the environment periodically.

28. The carbon monoxide monitor of claim 27 wherein a determined concentration of carbon monoxide is stored to memory.

29. The carbon monoxide monitor of claim 28 wherein the processor calculates the carboxyhemoglobin level estimated from ambient carbon monoxide concentrations calculated up to a predefined time period prior to the carboxyhemoglobin level calculation.

30. The carbon monoxide monitor of claim 26 wherein a signal is not provided by the processor if the estimated level of carboxyhemoglobin exceeds a threshold carboxyhemoglobin concentration and the estimated level of carboxyhemoglobin is less than the immediately preceding estimated level of carboxyhemoglobin.

31. The carbon monoxide monitor of claim 26 wherein the device is selected from the group consisting of an analog display, digital display, light emitting device, sound emitting device, shut-down device for the apparatus, or combination thereof.

32. The carton monoxide monitor of claim 26 wherein an output signal is provided at or above a specified carbon monoxide concentration threshold, the output signal activating a device selected from the group consisting of an analog display, digital display, light emitting device, sound emitting device, shut-down device for the apparatus, or combination thereof.

33. A system for monitoring carboxyhemoglobin levels of people in an environment for use with all apparatus emitting carbon monoxide, said system comprising:
a. a sensor for measuring oxygen saturation or carboxyhemoglobin levels in blood, said sensor providing a signal representative of the measured oxygen saturation or carboxyhemoglobin levels; and
b. a processor receiving and responsive to the signal for generating an output signal corresponding to estimated oxygen saturation or carboxyhemoglobin levels, said processor:
  i. receiving the signal from the sensor,
  ii. determining the oxygen saturation or carboxyhemoglobin levels corresponding to the signal,
  iii. providing an output signal at or above a specified carboxyhemoglobin level threshold.

34. The system of claim 33 further comprising a device that indicates a carboxyhemoglobin level at a specified output signal.

35. The system of claim 34 wherein the signals activate a device, wherein the device is an analog display, digital display, light emitting device, sound emitting device, shut-down device for the apparatus, or combination thereof.

36. The system of claim 33 wherein the processor calculates a period of time remaining until a predetermined carboxyhemoglobin level is reached.

37. The system of claim 33 wherein the oxygen saturation sensor is a pulse oximeter.

38. A carbon monoxide emitting apparatus having the carboxyhemoglobin level monitoring system of claim 33.

39. The system of claim 35, said processor:
a. receiving the signal from the sensor,
b. retrieving stored oxygen saturation or carboxyhemoglobin levels from memory,
c. determining the oxygen saturation or carboxyhemoglobin levels corresponding to the signal and stored oxygen saturation or carboxyhemoglobin levels,
d. storing determined oxygen saturation or carboxyhemoglobin level data to memory, and
e. providing an output signal at or above a specified carboxyhemoglobin level threshold;
wherein the stored oxygen saturation or carboxyhemoglobin levels are retained in memory for a predetermined period of time while the apparatus is shut off for retrieval and calculation of subsequent oxygen saturation or carboxyhemoglobin levels.

40. The system of claim 39 further comprising a device that indicates a carboxyhemoglobin level at a specified output signal.

41. The system of claim 40 wherein the signals activate a device, wherein the device is an analog display, digital display, light emitting device, sound emitting device, shutdown device for the apparatus, or combination thereof.

42. The system of claim 39 wherein the processor calculates a period of time remaining until a predetermined carboxyhemoglobin level is reached.

43. The system of claim 39 wherein the oxygen saturation sensor is a pulse oximeter.

44. A carbon monoxide emitting apparatus having the carboxyhemoglobin level monitoring system of claim 39.

45. The system of claim 39 the predetermined period of time is a workshift.

46. The system of claim 39 wherein the predetermined period of time is eight or more hours.

47. The system of claim 39 wherein the oxygen saturation or carboxyhemoglobin levels are calculated from stored oxygen saturation or carboxyhemoglobin levels determined before the apparatus was shut off and the oxygen saturation or carbon monoxide levels measured when the apparatus is restarted.

48. The carbon monoxide emitting apparatus of claim 39 wherein the apparatus is selected from the group consisting of a floor polisher and a power washer.

* * * * *